(12) United States Patent
Ehrenberger et al.

(10) Patent No.: US 8,821,156 B2
(45) Date of Patent: Sep. 2, 2014

(54) EXPANSION SCREW FOR REGULATING TEETH

(75) Inventors: Walter Ehrenberger, Kaempfelbach (DE); Simon Trautwein, Weingarten (DE)

(73) Assignee: Dentaurum GmbH & Co. KG, Inspringen (DE)

( * ) Notice: Subject to any disclaimer, the term of this patent is extended or adjusted under 35 U.S.C. 154(b) by 684 days.

(21) Appl. No.: 12/610,424

(22) Filed: Nov. 2, 2009

(65) Prior Publication Data
US 2010/0112507 A1 May 6, 2010

(30) Foreign Application Priority Data

Nov. 6, 2008 (DE) .......................... 10 2008 057 224

(51) Int. Cl.
*A61C 7/10* (2006.01)
(52) U.S. Cl.
CPC ....................................... *A61C 7/10* (2013.01)
USPC ................................................. 433/7; 433/18
(58) Field of Classification Search
CPC ............... A61C 7/06; A61C 7/10; A61C 7/36
USPC .............. 433/5–7, 18–19; 606/320, 325, 326, 606/57–58, 282, 105, 90; 623/17.17–17.18; 411/136, 147, 154, 160, 161, 539
See application file for complete search history.

(56) References Cited

U.S. PATENT DOCUMENTS

| 3,284,902 | A | * | 11/1966 | Dillberg et al. ................... 433/7 |
| 5,281,133 | A | * | 1/1994 | Farzin-Nia ........................ 433/7 |
| 5,472,344 | A | | 12/1995 | Binder et al. |
| 6,783,361 | B2 | * | 8/2004 | Huge et al. ........................ 433/7 |
| 7,384,265 | B2 | * | 6/2008 | Hanks ............................... 433/7 |
| 2007/0275341 | A1 | | 11/2007 | Hanks |
| 2008/0171300 | A1 | * | 7/2008 | Forster ............................. 433/7 |
| 2009/0081602 | A1 | * | 3/2009 | Ayan ................................ 433/7 |

FOREIGN PATENT DOCUMENTS

| DE | 43 38 986 | | 5/1994 |
| DE | 299 15 769 | | 4/2000 |
| DE | 10 2007 002 040 | | 7/2008 |
| EP | 0 596 986 | | 5/1994 |
| FR | 1 150 055 | | 1/1958 |
| GB | 483374 | * | 4/1938 |
| GB | 718385 | * | 10/1954 |

* cited by examiner

*Primary Examiner* — Cris L Rodriguez
*Assistant Examiner* — Edward Moran
(74) *Attorney, Agent, or Firm* — Leydig, Voit & Mayer, Ltd.

(57) ABSTRACT

An expansion screw for regulating teeth has two expansion-screw bodies, the spacing between which can be changed by means of a spindle, and has at least one guide pin which is aligned parallel to the spindle and engages in guide openings of the two expansion-screw bodies, the spindle having a first and a second threaded portion, each of which is connected to an expansion-screw body, and an actuating portion, with at least one point for application of a tool for rotating the spindle, and the expansion screw has a locking mechanism which interacts with the actuating portion in order to secure the spindle against unintended rotation. The locking mechanism has at least one locking element with a locking member which is disposed laterally alongside the actuating portion and subjects the actuating portion to an axial spring force when the spindle is rotated.

16 Claims, 3 Drawing Sheets

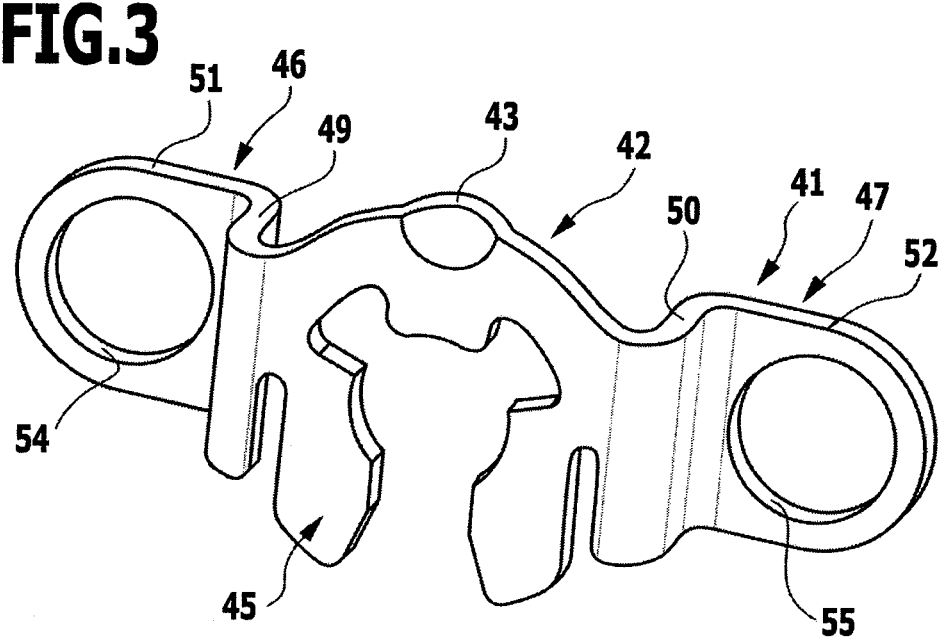
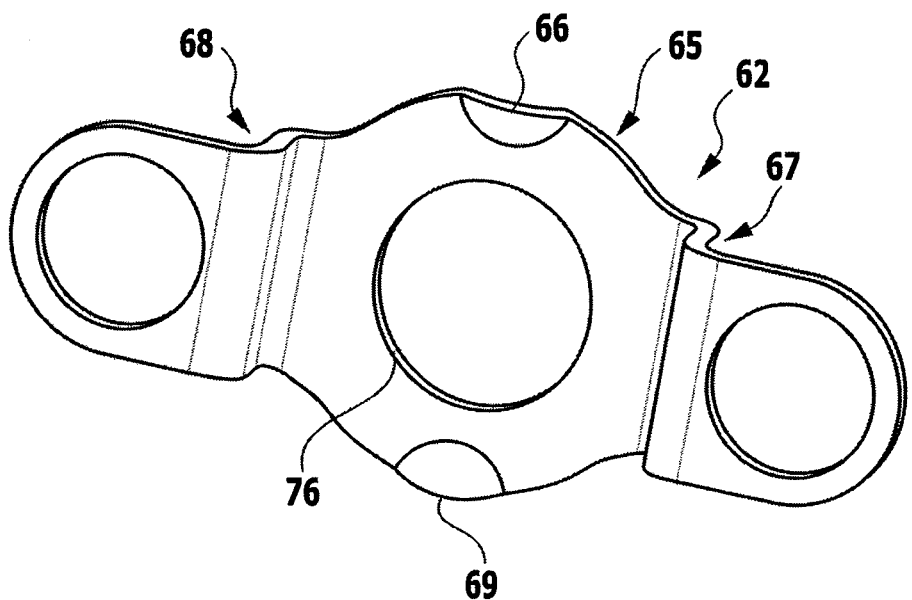

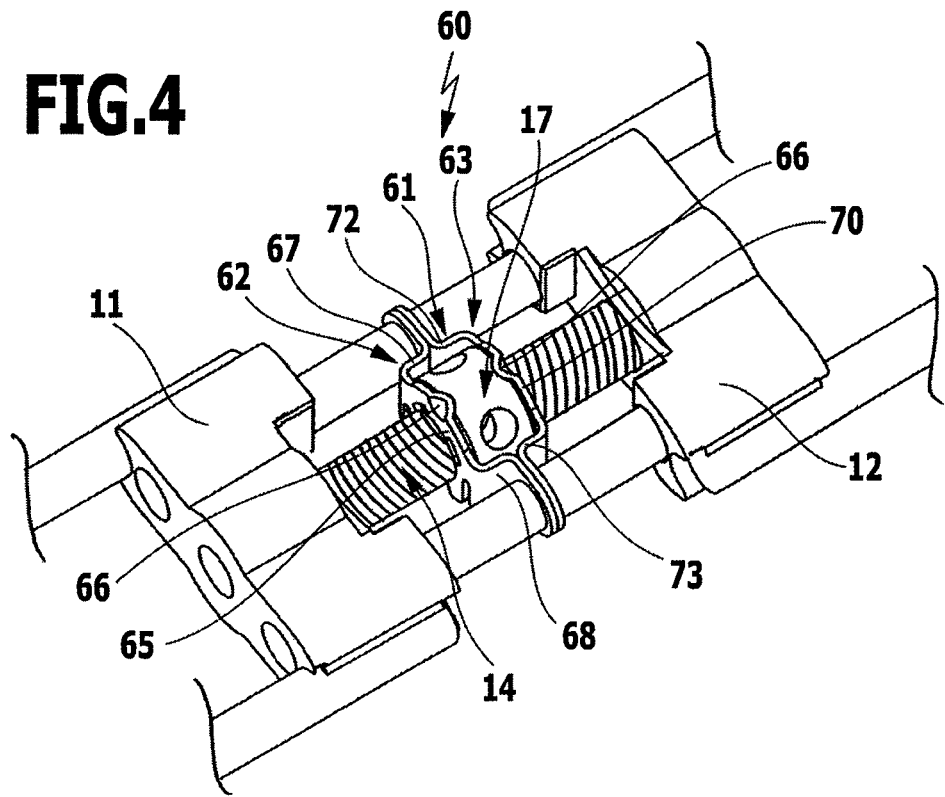
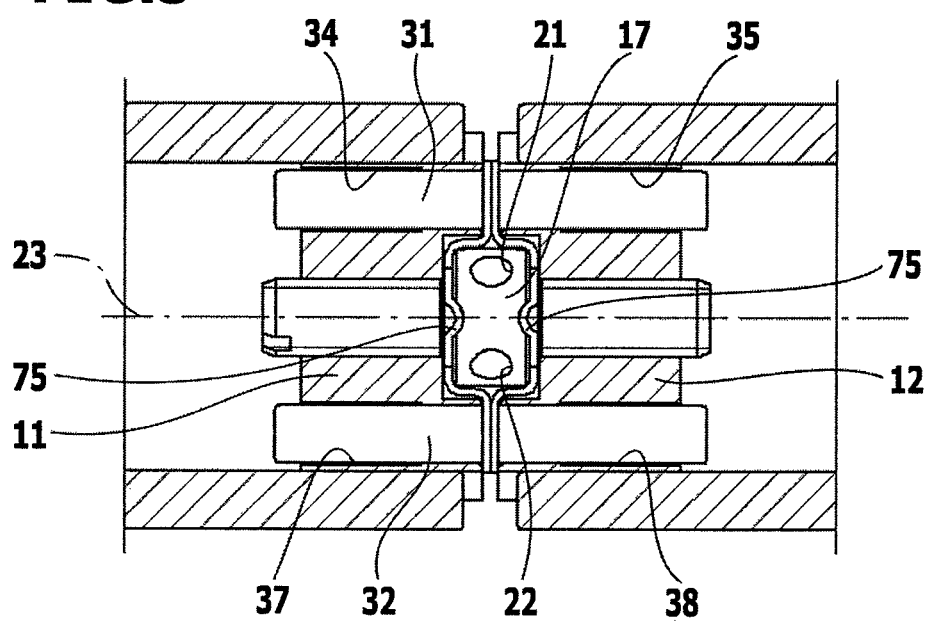

EXPANSION SCREW FOR REGULATING TEETH

The present disclosure relates to the subject matter disclosed in German application number 10 2008 057 224.1 of Nov. 6, 2008, which is incorporated herein by reference in its entirety and for all purposes.

BACKGROUND OF THE INVENTION

The invention relates to an expansion screw for regulating teeth, having two expansion-screw bodies, the spacing between which can be changed by means of a spindle, and having at least one guide pin which is aligned parallel to the spindle and engages in guide openings of the two expansion-screw bodies, the spindle having a first and a second threaded portion, each of which is connected to an expansion-screw body, and an actuating portion, with at least one point for application of a tool for rotating the spindle, and the expansion screw having a locking mechanism which interacts with the actuating portion in order to secure the spindle against unintended rotation.

An expansion screw of this kind is known from DE-A-10 2007 002 040. Rotating the spindle makes it possible to change the spacing which the two expansion-screw bodies assume in relation to one another, and the locking mechanism ensures that the spindle does not adjust of its own accord. The locking mechanism used in the known expansion screw is a metal strip which extends over the spindle, transversely to the longitudinal axis of the spindle, and is secured to the guide pins. It rests on the outer periphery of the actuating portion and acts as a friction brake, which makes it more difficult for the spindle to rotate. The actuating portion has a non-circular outer cross-section, so that the frictional force generated by the metal strip depends on the angle-of-rotation position of the spindle. The spindle can thus be secured against unintended rotation, but the expansion screw has not insignificant installation dimensions.

It is an object of the present invention to develop an expansion screw of the type mentioned in the introduction such that it has smaller installation dimensions.

SUMMARY OF THE INVENTION

This object is achieved according to the invention, in the case of an expansion screw of the generic type, in that the locking mechanism has at least one locking element with a locking member which is disposed laterally alongside the actuating portion and subjects the actuating portion to an axially aligned spring force when the spindle is rotated. The action of the locking member disposed laterally alongside the actuating portion prevents unintended rotation of the actuating portion, and thus also of the spindle as a whole. The locking member is disposed laterally alongside the actuating portion, that is to say at an end face of the actuating portion, as seen in relation to the axial direction of the spindle. The expansion screw can thus be produced with very small installation dimensions, and the outer periphery of the actuating portion is easily accessible both on the top side and on the underside of the expansion screw, so that the expansion screw can be actuated straightforwardly irrespective of its position in a patient's mouth.

It is advantageous if the locking member has at least one latching element which is adapted to be latched, in at least one angular position of the spindle, to a corresponding latching element disposed on an end face of the actuating portion. This makes it possible for the spindle to be arrested in a stepwise manner in that the spindle assumes an angular position such that the latching element disposed on the locking member interacts with a corresponding latching element, which is disposed on the end face of the actuating portion, in order to make a latching connection.

It may be provided that at least one end face of the actuating portion has disposed on it a plurality of latching elements which are spaced apart from one another at uniform angular spacings. For example, it may be provided that at least one end face of the actuating portion has disposed on it a total of four latching elements, each at an angular spacing of 90° from one another, so that the actuating portion can be arrested by means of the interacting latching elements following a quarter rotation in each case.

The at least one latching element of the locking member is preferably configured as a latching protrusion and the at least one latching element of the actuating portion is preferably configured as a latching indentation which is disposed on an end face of the actuating portion and into which the latching protrusion of the locking member penetrates. Of course, a complementary configuration is also conceivable such that the actuating portion has disposed on an end face at least one latching protrusion which interacts with a latching indentation on the locking member. Stepwise arresting of the spindle can always be achieved in a constructionally simple manner by the provision of at least one latching protrusion and a corresponding latching indentation.

It is advantageous if the at least one latching element of the locking member forms a positive lock with the at least one latching element of the actuating portion. Providing a positive lock makes it possible to achieve a particularly effective locking action which secures the spindle against unintended rotation.

Particularly small installation dimensions are achieved, in the case of an advantageous configuration of the expansion screw according to the invention, by the locking element being produced from a flat material.

In particular, it may be provided that the locking element is produced from sheet metal. When the spindle is rotated, the flat material, in particular the sheet metal, can be deformed elastically to the extent where, by virtue of a tool, for example, a pin, being applied, the spindle can be readily rotated, unintended rotation of the spindle being however prevented on account of the spring force exerted by the flat material.

In order for the locking element to be secured axially on the spindle, an advantageous embodiment provides that the spindle has an annular groove laterally alongside the actuating portion, into which groove the locking element penetrates.

It is advantageous in respect of straightforward installation and axial securing of the locking element on the spindle if the locking element is adapted to be latched to the spindle.

The locking element preferably has a U-shaped or C-shaped bracket which accommodates the spindle. In particular, it may be provided that the bracket penetrates into the annular groove. The annular groove preferably latches into the bracket.

The locking element advantageously comprises at least one retaining arm which projects outward from the locking member and is retained on a guide pin.

It may be provided that the at least one retaining arm has an opening through which a guide pin engages. The opening may be formed, for example, in the form of a punched-out portion.

The at least one retaining arm is preferably fixed in an axially immovable manner on a guide pin. In particular, it may be provided that the retaining arm is connected by bonding action, for example welded or adhesively bonded, to the guide pin.

In a particularly preferred embodiment of the expansion screw according to the invention, this expansion screw has two guide pins, between which the spindle is disposed, and the locking member forms a central portion of the locking element, and this central portion is disposed on the spindle and subjects the actuating portion to an axial spring force when the spindle is rotated, the locking element having first and second retaining arms which are directed away from one another, adjoin the central portion and are each retained in captive fashion on a guide pin. Retaining arms may be, for example, welded or adhesively bonded to the respective guide pin.

The two retaining arms are advantageously each of L-shaped configuration and comprise a first, axially oriented portion and a second, radially oriented portion. The axially oriented portion runs parallel to the longitudinal axis of the spindle, and the radially oriented portion runs perpendicularly to the longitudinal axis of the spindle. The radially oriented portions may each be fixed to a guide pin. For this purpose, they may each have an opening through which the respective guide pin engages.

The spindle is secured particularly reliably against unintended rotation, in the case of an advantageous embodiment, in that the locking mechanism has two locking elements, the locking members of which are each disposed laterally at an end face of the actuating portion and subject the actuating portion to an axial spring force in each case when the spindle is rotated.

The two locking elements are preferably configured in a mirror-symmetrical manner in relation to one another.

A particularly compact construction is ensured, in the case of an advantageous embodiment, in that the two locking elements fully enclose the actuating portion as seen in plan view. For this purpose, the two locking elements may each have a locking member that is disposed at an end face of the actuating portion, and two L-shaped retaining arms. The axially oriented portions of the retaining arms, together with the locking member, form a U shape, which accommodates half of the actuating portion, and the provision of two locking elements results in the actuating portion being enclosed fully by parts of the locking elements.

In particular when use is made of two locking elements which accommodate the actuating portion of the spindle between them, it is advantageous if the two locking elements each have a central through-passage opening through which the spindle engages, and if the locking elements are each secured on at least one guide pin.

In particular the expansion screw may have two guide pins, between which the spindle is disposed, and the two locking elements may have, in their end regions, a respective opening through which a guide pin engages and, in a central region, the locking elements may each have a central through-passage opening through which the spindle engages. At their end openings, the locking elements are preferably welded to the guide pins. Since the locking elements accommodate the actuating portion between them, an axially non-displaceable arrangement of the locking elements on the spindle that engages through the central through-passage openings is also ensured without use having to be made of any snap-fit or latching connection between the locking elements and the spindle. All that is required for installation of the locking elements is for these to be pushed in opposite directions onto the guide pins and the spindle until they each engage against an end face of the actuating portion, and they can then be connected by bonding action, in particular welded, to the guide pins.

The following description of preferred embodiments of the invention serves for a more detailed explanation in conjunction with the drawings.

BRIEF DESCRIPTION OF THE DRAWINGS

FIG. 3: shows a perspective illustration of a locking element of the expansion screw from FIG. 1;

FIG. 4: shows a perspective illustration of a second embodiment of an expansion screw according to the invention;

FIG. 5: shows a longitudinal-section view of the expansion screw from FIG. 4; and FIG. 6: shows a perspective illustration of a locking element of the expansion screw from FIG. 4.

DETAILED DESCRIPTION OF THE INVENTION

Figure 1:
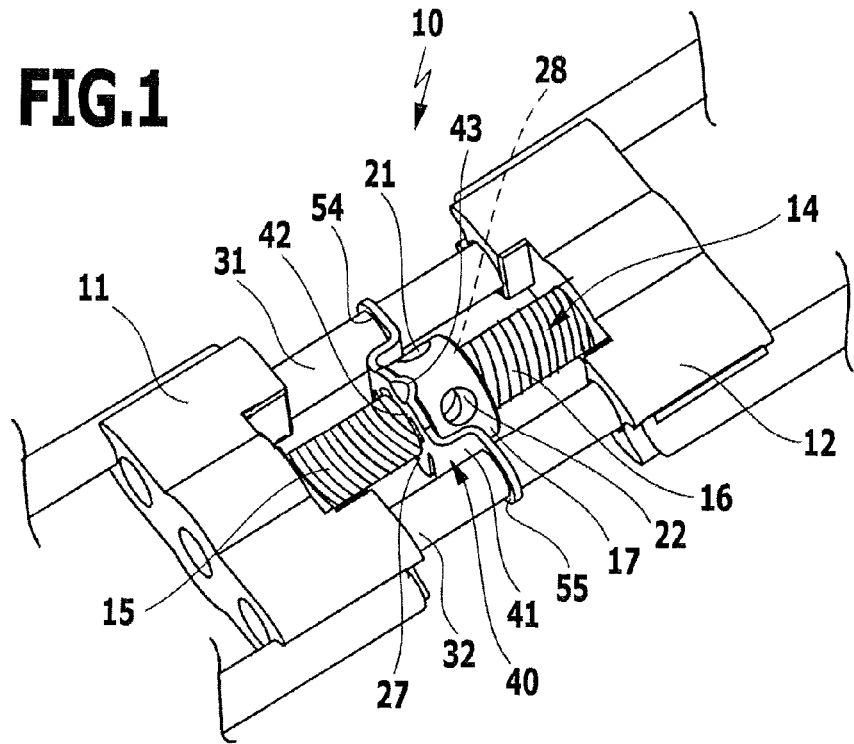
FIG. 1: shows a perspective illustration of a first embodiment of an expansion screw according to the invention.
Figure 2:
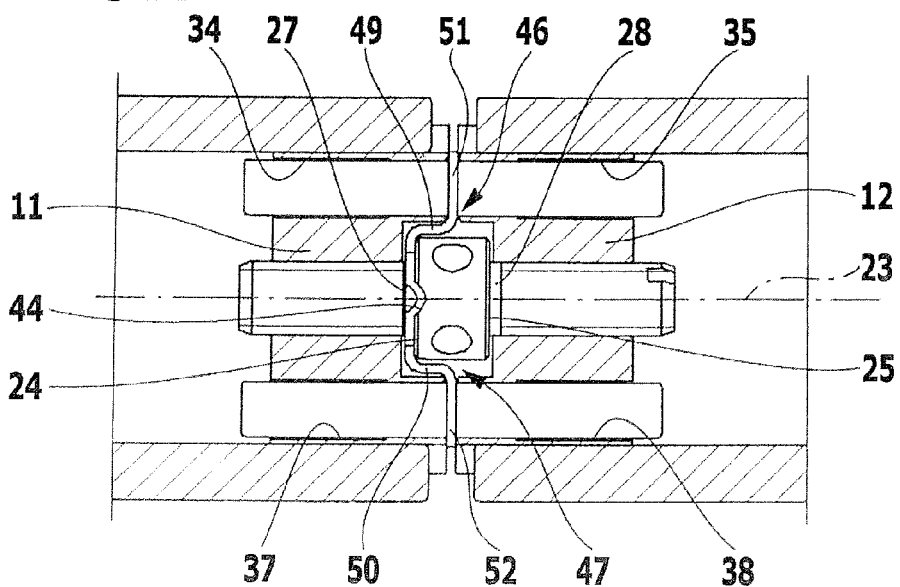
FIG. 2: shows a longitudinal-section view of the expansion screw from FIG. 1.

In FIGS. 1, 2 and 3, there is illustrated a first embodiment of an expansion screw according to the invention, designated as a whole by reference numeral 10. It comprises a first expansion-screw body 11 and a second expansion-screw body 12, which are connected to one another via a spindle 14. The spindle 14 has a first threaded portion 15 and a second threaded portion 16, between which a widened actuating portion 17 is disposed. The two threaded portions 15 and 16 each have an external thread with opposite directions of rotation. The threaded portions 15 and 16 each penetrate into a bore, with matching internal thread, in the expansion-screw bodies 11 and 12, respectively.

The actuating portion 17 is circular-cylindrical and has two through-passage bores 21, 22 which are offset in relation to one another by 90°, each forming a point for application for a pin-like tool for rotating the spindle 14. By means of its region which projects radially, as seen in relation to the longitudinal axis 23 of the spindle 14, beyond the threaded portions 15 and 16, the actuating portion 17 forms a first end face 24, which is directed toward the first expansion-screw body 11, and a second end face 25, which is directed toward the second expansion-screw body 12. Directly adjacent the end faces 24 and 25, the threaded portions 15 and 16 have a first annular groove 27 and a second annular groove 28, respectively.

A first guide pin 31 and a second guide pin 32 run parallel to the spindle 14, the spindle 14 being disposed between them. By means of its end regions, the first guide pin 31 penetrates into guide openings 34 and 35 of the first expansion-screw body 11 and of the second expansion-screw body 12, respectively, and the second guide pin 32 penetrates, by means of its end regions, into corresponding guide openings 37 and 38 of the two expansion-screw bodies 11 and 12. In the case of the embodiment illustrated, the guide pins 31 and 32 are circular-cylindrical, but they could also have some other cross-section, that is to say they could also be of prismatic configuration.

Rotating the spindle 14 by means of a suitable tool, which acts on the actuating portion 17, makes it possible to change the spacing which the two expansion-screw bodies 11 and 12 assume in relation to one another. In order to avoid unintended rotation of the spindle 14, the expansion screw 10 has a locking mechanism 40 with a single locking element 41, which is in the form of a sheet-metal part produced by bending and punching. The locking element 41 is illustrated on an enlarged scale in FIG. 3. It has a central portion which forms a locking member 42 that engages against the first end face 24 of the actuating portion 17. The locking element is of substantially U-shaped configuration and forms a latching forked portion or bracket 45 into which the first annular groove 27 latches. In the center, above the latching bracket 45, the locking member 42 has a latching protrusion 43 which, in the angular position of the spindle 14 which is illustrated in FIGS. 1 and 2, penetrates in a positively locking manner into a complementary latching indentation 44 in the actuating portion 17. The latching indentation 44 is disposed on the first end face 24. The latching protrusion 43, like the latching indentation 44, has an arcuate shape, so that the spindle 14 can readily be rotated, by means of a suitable tool, out of the angular position illustrated in FIGS. 1 and 2, the locking member 42, in the region of the latching protrusion 43, then being deformed elastically in the direction away from the first end face 24 and thus subjecting the first end face 24 of the actuating portion 17 to an elastic spring force. The locking member 42 thus secures the spindle 14 against unintended rotation.

As has already been explained, the locking member 42 forms the central portion of the sheet-like locking element 41. The locking member 42 is adjoined, in the direction of the first guide pin 31, by a first retaining arm 46 and, in the direction of the second guide pin 32, the locking member 42 is adjoined by a second retaining arm 47. The two retaining arms are each bent in an L-shaped manner and comprise a first portion 49, 50, running parallel to the longitudinal axis 23 of the spindle 14, and a second portion 51, 52, running perpendicularly to the longitudinal axis 23. The two second portions 51 and 52 each have an opening in the form of a respective circular punched-out portion 54, 55 through which the respective guide pin 31, 32 engages. In the region of the punched-out portions 54 and 55, the respective retaining arms 46 and 47 are each connected by bonding action to a respective guide pin 31, 32. In the embodiment illustrated, they are welded to the respective guide pin 31, 32. The weld connection ensures that the locking element 41 is retained in captive fashion on the guide pin 31, 32.

As a result of the locking member 42 being disposed laterally alongside the first end face 24 of the actuating portion 17, the spindle 14 can be secured reliably against unintended rotation without the expansion screw 10 thereby taking on large installation dimensions. Rather, the expansion screw 10 has comparatively small installation dimensions, but it is nevertheless ensured that the spindle 14 can be rotated only as a result of a spring force to which the actuating portion 17 is axially subjected being overcome.

FIGS. 4, 5 and 6 illustrate a second embodiment of an expansion screw according to the invention, this being designated overall by the reference numeral 60. This is of largely identical configuration to the expansion screw 10, which has been explained above with reference to FIGS. 1, 2 and 3. For identical components, the same reference numerals are thus used in FIGS. 4, 5 and 6 as in FIGS. 1, 2 and 3. As far as these reference numerals are concerned, in order to avoid repetition, reference is made to the explanations given above.

The expansion screw 60 differs from the expansion screw 10 by use being made of a locking mechanism 61 with two locking elements 62 and 63 which secure the spindle 14 of the expansion screw 60 against unintended rotation. The locking element 62 is illustrated on an enlarged scale in FIG. 6. It is largely identical to the locking element 41 explained above. It comprises a locking member 65, disposed at the first end face 24 of the actuating portion 17, and a first retaining arm 67 and a second retaining arm 68, which are bent in an L-shaped manner and each have, at their free end regions, a punched-out portion through which a respective guide pin 31, 32 engages. In the region of the punched-out portions, the retaining arms 67 and 68 are welded to the respective guide pin 31, 32. In contrast to the locking element 41, the locking member 65 of the locking element 62 does not have a latching bracket into which the spindle 14 latches by way of an annular groove; rather, the latching member 65 comprises a central through-passage opening 76 through which the spindle 14 of the expansion screw 60 engages. The locking element 62 can thus be pushed axially onto the spindle 14. Moreover, the through-passage opening 76 allows the locking member 65 to be provided with two latching protrusions 66, 69 located diametrically opposite one another.

The second locking element 63 is mirror-symmetrical to the first locking element 62. It has a central portion which is formed as a locking member 70 and has a central through-passage opening 76 and latching protrusions 66, 69, and the locking member 70 is adjoined, in the direction toward the first guide pin 31, by a first retaining arm 72 and, in the direction toward the second guide pin 32, by a second retaining arm 73. The two retaining arms 72 and 73 are also bent in an L-shaped manner and have, at their free end regions, a punched-out portion through which a respective guide pin 31, 32 engages. At the punched-out portions, the second locking element 63 is welded to the guide pins 31, 32.

In order to make a latching connection between the locking member 70 and the actuating portion 17, the latter, in the embodiment illustrated in FIGS. 4, 5 and 6, has not just on its first end face 24, but also on its second end face 25, latching indentations 75 which are configured to complement the latching protrusions 66 and 69 and form a positive lock with a respective latching protrusion 66, 69 when the spindle 14 of the expansion screw 60 assumes the angular position illustrated in FIGS. 4 and 5. If the spindle 14 is rotated out of this angular position, then the latching protrusions slide out of the respective latching indentations of the actuating portion 17 and subject the actuating portion 17, from both sides, to an axially directed spring force which secures the spindle 14 of the expansion screw 60 against unintended rotation.

For installation, the two locking elements 62, 63 starting from one end of the spindle 14 in each case, are pushed axially onto the spindle 14 until the locking elements engage against the end faces 24 and 25 of the actuating portion 17 and accommodate the same between them. The guide pins 31 and 32 can then be guided through the punched-out portions of the locking elements 62 and 63 that engage against one another with face-to-face contact at the ends, and welded to the locking elements 62, 63.

It is also the case that the expansion screw 60 has comparatively small installation dimensions, but nevertheless the spindle 14 of the expansion screw 60 can be rotated only as a result of axially active spring forces being overcome.

The invention claimed is:

1. An expansion screw for regulating teeth, having two expansion-screw bodies and a spindle, and spacing between the bodies, the spacing between which can be changed by means of the spindle, and at least one guide pin which is aligned parallel to the spindle and engages guide openings of the two expansion-screw bodies, the spindle having a first threaded portion and a second threaded portion, each of which is connected to an expansion-screw body, and an actuating portion, with at least one point for application of a tool for rotating the spindle, and the expansion screw having a locking mechanism which interacts with the actuating portion in order to secure the spindle against unintended rotation, wherein the locking mechanism has at least one locking element with a locking member which is disposed laterally alongside the actuating portion and subjects the actuating portion to a spring force that is axially aligned with respect to the longitudinal axis of the spindle when the spindle is rotated, and the locking member has at least one latching element which is adapted to be latched, in at least one angular position of the spindle, to a corresponding latching element disposed on an axial end face of the actuating portion.

2. The expansion screw according to claim 1, wherein at least one end face of the actuating portion has disposed on it a plurality of latching elements which are spaced apart from one another at uniform angular spacings.

3. The expansion screw according to claim 1, wherein the at least one latching element of the locking member is configured as a latching protrusion, and wherein at least one latching element of the actuating portion is configured as a latching indentation which is disposed on an end face of the actuating portion and into which the latching protrusion penetrates.

4. The expansion screw according to claim 1, wherein the at least one latching element of the locking member forms a positive lock with the at least one latching element of the actuating element.

5. The expansion screw according to claim 1, wherein the locking element is produced from a flat material.

6. The expansion screw according to claim 1, wherein the locking element comprises sheet metal.

7. The expansion screw according to claim 1, wherein the spindle has an annular groove laterally alongside the actuating portion, into which groove the locking element penetrates.

8. The expansion screw according to claim 1, wherein the locking element has a U-shaped or C-shaped bracket which encompasses the spindle.

9. The expansion screw according to claim 1, wherein the locking element has at least one retaining arm which projects outward from the locking member and is retained on the guide pin.

10. The expansion screw according to claim 9, wherein the at least one retaining arm has an opening through which the guide pin engages.

11. The expansion screw according to claim 9, wherein the at least one retaining arm is fixed in an axially immovable manner on a guide pin.

12. The expansion screw according to claim 1, wherein the expansion screw has two guide pins, between which the spindle is disposed, and wherein the locking member forms a central portion of the locking element, and this central portion is disposed on the spindle and subjects the actuating portion to an axial spring force when the spindle is rotated, and wherein the locking element has first and second retaining arms which are directed away from one another, adjoin the central portion and are each retained in captive fashion on a guide pin.

13. The expansion screw according to claim 12, wherein the two retaining arms are each of L-shaped configuration and have a first, axially oriented portion and a second, radially oriented portion.

14. The expansion screw according to claim 1, wherein the locking mechanism has two locking elements, the locking members of which are each disposed laterally at an end face of the actuating portion and subject the actuating portion to an axial spring force in each case when the spindle is rotated.

15. The expansion screw according to claim 14, wherein the two locking elements encompass the actuating portion between them.

16. The expansion screw according to claim 15, wherein the locking elements each have a central through-passage opening through which the spindle engages, and wherein the locking elements are each secured on at least one guide pin.

* * * * *